United States Patent [19]

Clark, II

[11] 4,321,918

[45] Mar. 30, 1982

[54] PROCESS FOR SUPPRESSING IMMUNITY TO TRANSPLANTS

[76] Inventor: William T. Clark, II, 6 Davis Blvd., New Orleans, La. 70121

[21] Appl. No.: 87,576

[22] Filed: Oct. 23, 1979

[51] Int. Cl.³ .............................................. A61M 1/03
[52] U.S. Cl. ................................. 128/214 R; 128/362
[58] Field of Search .................... 128/1 R, 214 R, 1.1, 128/395, 362, 396; 250/430, 432 R, 435, 437

[56] References Cited

U.S. PATENT DOCUMENTS

| | | | |
|---|---|---|---|
| 1,683,877 | 9/1928 | Edblom et al. ...................... | 128/395 |
| 2,992,329 | 7/1961 | Jeppson ............................... | 250/437 |
| 3,929,130 | 12/1975 | Hargest ............................... | 128/214 R |
| 4,061,741 | 12/1977 | Hyden et al. ...................... | 128/214 R |

OTHER PUBLICATIONS

Cronkite et al., "New England Journal of Medicine" vol. 272, No. 9, pp. 456–461.
Slatkin et al., "Radiation Research" vol. 19, 1963, p. 409.
Cronkite et al., "Blood" vol. 20, No. 2, Aug. 1962.
Jansen et al., "Blood" , vol. 20, No. 4, Oct. 1962.
Sipe et al., "Radiation Research" vol. 25, 1965, pp. 684–694.
Thomas et al., "New England Journal of Medicine" , Jul. 1, 1965, pp. 6–12.
Lajtha et al., "The Lancet", Feb. 17, 1962, pp. 353–355.
Extracorporeal Irradiation of the Blood, L. M. Schiffer, et al., Seminars in Hematology, vol. 3, No. 2, (Apr. 1966).

Primary Examiner—William E. Kamm
Attorney, Agent, or Firm—James H. Littlepage

[57] ABSTRACT

In order to inhibit rejection of transplants in humans, lymphoctyes are suppressed by limited and closely controlled extracorporeal irradiation of an intensity and duration sufficient to reduce lymphocyte function to from about 10% to about 20% of normal.

6 Claims, 3 Drawing Figures

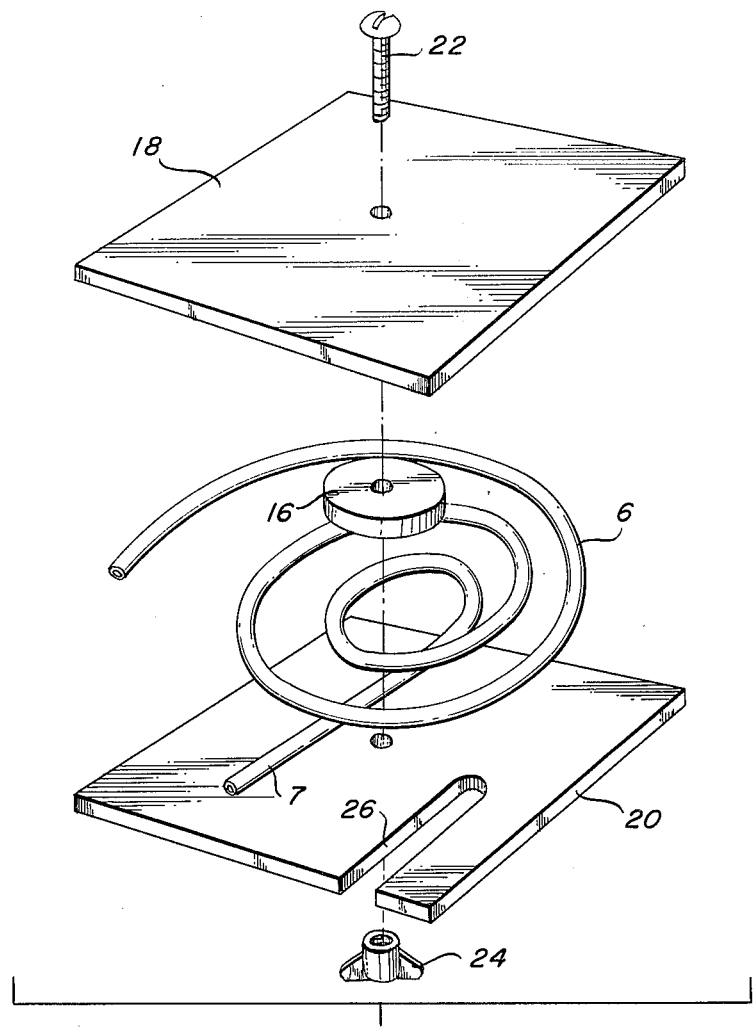
Fig. 2
Fig. 3
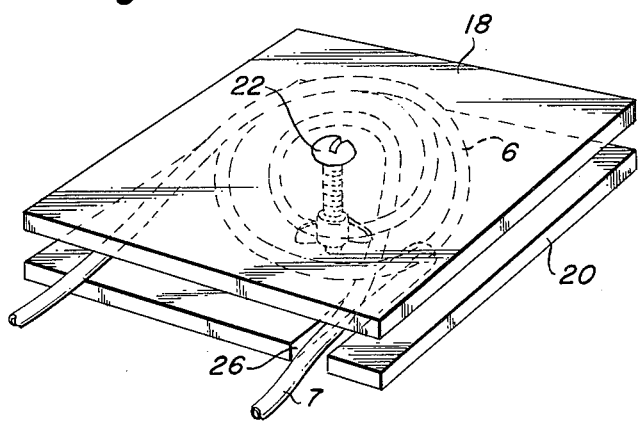

PROCESS FOR SUPPRESSING IMMUNITY TO TRANSPLANTS

OBJECTS AND DEFINITIONS

The purpose of this invention is to provide a means of extracorporeal irradiation of the blood in order to suppress circulating immune factors present in the blood of a living person. A particular use of the invention is to suppress immunity in patients who have received organ transplants.

Direct X-radiation of the transplanted organ is known to suppress transplant rejection, but such direct radiation is dose-limited because of secondary radiation damage to surrounding tissues and to the organ itself. Extracorporeal irradiation of the blood poses no such hazard to tissues and can suppress circulating immune factors. Previous attempts to suppress rejection by this method were unsuccessful because of inadequate apparatus and technique.

The subject extracorporeal irradiation process can thwart a rejection crisis. Clinical trials have shown that the patient suffers no discomfort and no apparent aftereffects from a simple procedure which usually lasts less than an hour. When rejection symptoms recur, the procedure can be repeated without cumulative hazard. Hazardous immunosuppressant drugs can be reduced, and the patient's health and well being improve.

The concept and operation of the invention is simple and straightforward. A length of sterile tubing is wound into a flat spiral disc. This spiral disc is the extracorporeal blood pathway which is exposed to the radiation field.

If the X-ray output is known, and the blood volume of the tubing is known, then the actual received radiation dose can be calculated for any blood flow rate through the tubing. Doses can then be delivered sufficient to suppress immune factors or other elements according to their radiosensitivity.

The dose received by the blood as it traverses the radiation field may be referred to as the Transit Dose. The Transit Dose is determined by dividing the X-ray output (Dose Rate) by a Transit Factor. The Transit Factor is equal to the blood flow rate divided by the volume of the extracorporeal blood pathway (Link Volume). By formula:

$$\text{Transit Time (Seconds)} = \frac{60}{\left(\frac{\text{flow rate}}{\text{link volume}}\right)}$$

$$\text{Transit Dose Factor} = \frac{\text{flow rate}}{\text{link volume}}$$

$$\text{Transit Dose} = \frac{\text{Dose Rate}}{\text{Transit Dose Factor}} \text{ or}$$

$$\text{Dose Rate} = \frac{\text{flow rate}}{\text{link volume}} \times \text{transit dose}$$

For example, using tubing 100 cm long, wound in a 10 cm spiral, with a 20 cc volume, at a blood flow rate of 100 ml/min.:

Transit Time = 12 seconds Transit Dose Factor = 5

Therefore, for a Dose Rate of 155.5 R/min: Transit Dose = 31.1 R/min.

The flat spiral disc presents a substantially uniform field to the radiation beam. This is essential for accurate dose calculations. Therefore, for a substantially uniform field:

$$\text{Transit Dose} = \frac{\text{link volume}}{\text{flow rate}} \times \text{Dose Rate}$$

The Total Dose is determined by multiplying the Transit Dose by the number of times the patient's blood volume has passed through the radiation field (exchanged). One exchange is usually sufficient. For example: at a flow rate of 100 ML/min, a blood flow volume of 3.5 liters will exchange in 35 minutes (disregarding mixture).

Therefore: Total Dose = Exchanges × Transit Dose

These and other objects will be apparent in the following specification and drawings in which:

FIG. 2 is a exploded view of the spiral tubing disc and mounting; and

FIG. 3 is a perspective view of the mounted spiral tubing disc.

Figure 1:
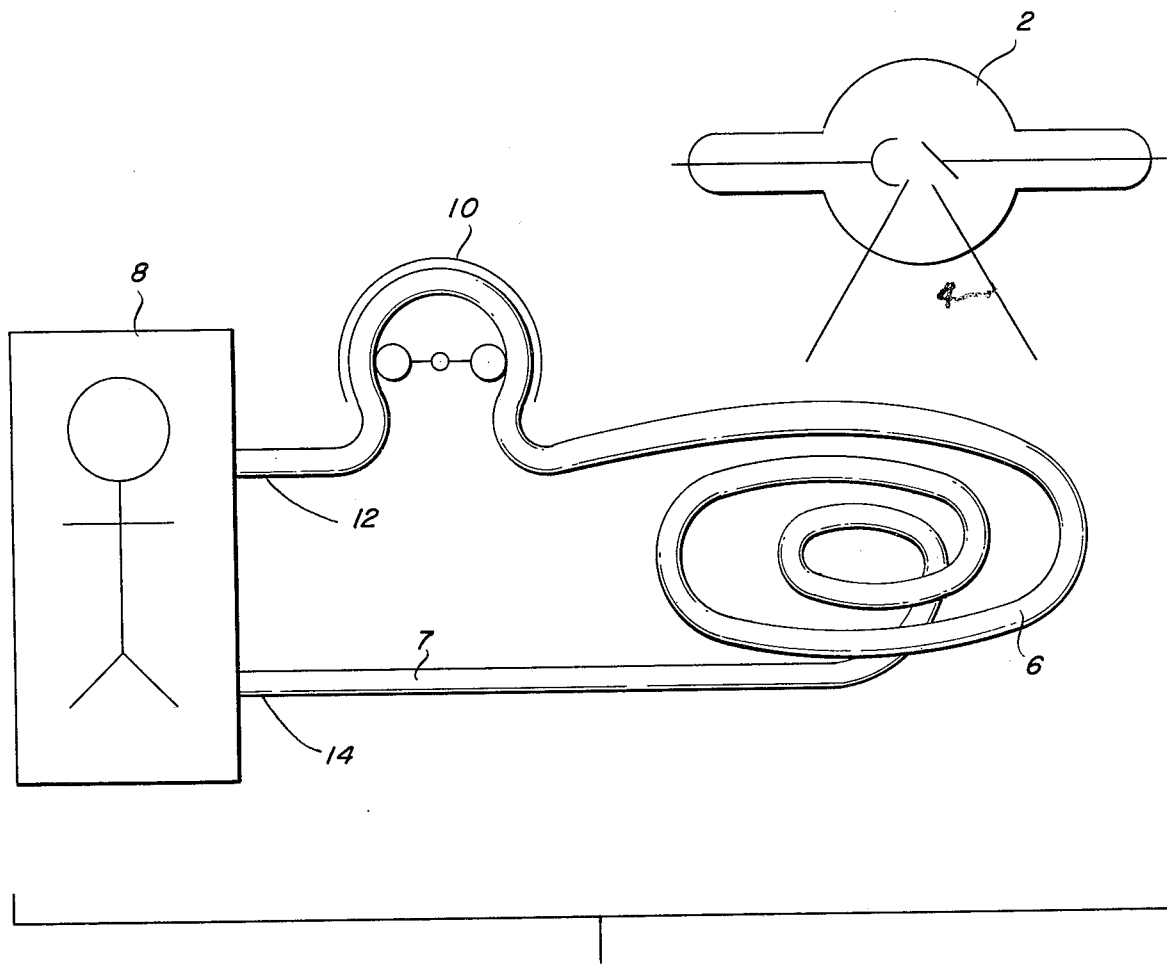
FIG. 1 is a diagram of the apparatus.

Referring to the drawings, FIG. 1, illustrates a source of X-rays 2 emitting a beam 4 which impinges upon the spiral disc 6 of tubing 7. The patient 8 is cannulated so that a blood pump 10 can pump from an artery 12 through the spiral disc 6 and back to the patient's vein 14.

Referring to FIG. 2, the tubing 7 of spiral disc 6 is wound onto a bobbin 16 between two low-density plastic plates (polycarbonate, for example) 18 and 20 which keep the tubing flat and thereby keep the field substantially uniform. A screw 22 and a wing nut 24 keep the assembly together; a relief slot 26 for the tubing end allows the disc to remain flat. The spiral disc assembly may simply slide into a drawer in a shielded box beneath the source of radiation. The spiral may be wound in multiple layers in order to increase the radiation dose permitting a faster flow rate. The apparatus is shown assembled at FIG. 3.

The tubing used for extracorporeal irradiation is primed with normal saline and heparin before connection to the patient. The patient is then systemically heparinized and connected to the tubing via conventional cannulation with arteriovenous shunt or fistula.

The tubing 7 used for the extracorporeal irradiation link is any tubing suitable for an extracorporeal blood circuit and capable of allowing the passage of X-rays. For example, sterilized polyvinyl chloride tubing is suitable.

Ten renal rejection patients have been given a full course of treatment with the extracorporeal irradiation link. An eleventh patient (#7 on chart below) was started, but was mentally unwell and refused further treatment. Without treatment she rejected violently and expired. All remaining ten patients were given a full course of extracorporeal irradiation and all cases of rejection were stopped by this treatment. Prior to extracorporeal irradiation all patients were given immunosuppressant therapy to no avail. Patients were generally characterized by feeling unwell, rising blood pressure, rising BUN and creatinine, reduced urine output, and by immunological laboratory confirmation of rejection. After extracorporeal irradiation BUN and creatinine levels fell, blood pressure reduced, urine output rose, and immunological studies showed a sharp drop in lymphocyte function, with only 10 to 20% of the lymphocytes functional. Patients then had a general feeling of well being. Those patients who experienced repeat episodes of rejection were again treated with extracorporeal irradiation and the rejection was stopped in each case. The patient summaries are listed below.

| Patient | Age | Sex | Episodes | Treatments | Rejection Stopped? |
|---|---|---|---|---|---|
| 1.JJ | 49 | M | 3 | 15 | yes |
| 2.VL | 20 | M | 2 | 8 | yes |
| 3.TM | 17 | M | 2 | 12 | yes |
| 4.AC | 23 | F | 2 | 7 | yes |
| 5.CH | 12 | F | 1 | 2 | yes |
| 6.RH | 25 | M | 1 | 4 | yes |
| 7.EL | 30 | F | 1 | | Withdrawn |
| 8.LA | 30 | M | 1 | 13 | yes |
| 9.JA | 44 | F | 1 | 8 | yes |
| 10.BG | 26 | M | 1 | 7 | yes |
| 11.MD | 13 | M | 1 | 6 | yes |

In the foregoing examples, the X-ray machine used was a G.E. Maxima R with a ½ mm. Al. filter, operated at 100 kv with a 7 ma. current delivering a dose rate of 155.5 R/min. to the tubing spiral disposed at 15 cm from the target electrode. The resultant transit doses were 31.1 R per minute. In each instance, after each treatment the patient's blood was given a standard Lymphocyte Stimulation Test, and the irradiation was considered to be adequate when only from 10% to 20% of the lymphocytes functioned normally. If substantially more than 20% of the lymphocytes functioned normally, the patient's rejection would continue uninhibited; and if substantially less than 10% of the lymphocytes functioned normally, the patient's system would tend to be triggered into creating an excessive number of lymphocytes, and the rejection process would be so accelerated. The treatments of a patient are continued from day-to-day until the rejection subsides.

Because of the relatively short life span of the blood of a human being, the cumulative effects of the extracorporeal X-ray irradiation are not a factor, as it is when other tissues are irradiated. Therefore, the blood which has been irradiated during one rejection episode will not normally be present during the treatment of a subsequent episode.

Total doses per treatment ranging from 24.4 R to 93.3 R have been sufficient to reduce lymphocyte function to from 10% to 20% of normal. A reduction of lymphocyte function to the range of about 10% to 20% normal seems to suppress lymphocyte function without hurting them.

Ordinarily after a patient has undergone immunosuppressant therapy, he is very vulnerable to attack by many kinds of disease organisms. Observation of patient and undergoing the subject treatment show that the number of lymphocytes has not reduced and, in some instances the actual number has increased but their normal function has been reduced. Hence they are subsequently available to provide immunity from other diseases.

I claim:

1. A process for inhibiting immunity to a transplant in a human patient undergoing rejection symptoms which comprises:

exchanging the patient's blood through an extracorporeal link, and irradiating the patient's blood while in transit through the link with a transit dose to significantly reduce lymphocyte function but less than that required to significantly diminish the patient's lymphocyte population until the rejection symptoms subside.

2. A process for inhibiting immunity to a transplant in a human patient which comprises suppressing lymphocyte function in the patient's blood by exchanging the blood through an extracorporeal irradiation link, and treating the patient's blood by irradiating the same with X-rays until lymphocyte function is reduced to from about 10% to 20% of normal, wherein the blood is irradiated at a predetermined transit dose as a determined by the formula:

$$\text{Transit Time (secs.)} = \frac{60}{\left(\frac{\text{flow rate}}{\text{link volume}}\right)}$$

$$\text{Transit Dose Factor} = \frac{\text{flow rate}}{\text{link volume}}$$

$$\text{Transit Dose} = \frac{\text{Dose Rate}}{\text{Transit Dose Factor}}$$

or $$\text{Dose Rate} = \frac{\text{flow rate}}{\text{link volume}} \times \text{transit dose}$$

3. A process as claimed in claim 2, wherein the total dose is of a predetermined limited extent as determined by the formula:

Total Dose = Exchanges × Transit Dose.

4. A process as claimed in claim 3 wherein the total dose is between 24.4 R to 93.3 R.

5. A process for inhibiting immunity to a transplant in a human patient which comprises suppressing lymphocyte function in the patient's blood by treating the blood by changing the same through an extracorporeal irradiation link, irradiating the blood with X-rays while in transit through the link with a transit dose of about 31.1 R/min. as determined by the formula:

$$\text{Transit Time (secs.)} = \frac{60}{\left(\frac{\text{flow rate}}{\text{link volume}}\right)}$$

$$\text{Transit Dose Factor} = \frac{\text{flow rate}}{\text{link volume}}$$

$$\text{Transit Dose} = \frac{\text{Dose Rate}}{\text{Transit Dose Factor}}$$

or $$\text{Dose Rate} = \frac{\text{flow rate}}{\text{link volume}} \times \text{transit dose}$$

6. A process as claimed in claim 5, wherein the total dose per treatment is from 24.4 R to 93.3 R as determined by the formula:

Total Dose = Exchanges × Transit Dose.

* * * * *

UNITED STATES PATENT AND TRADEMARK OFFICE
CERTIFICATE OF CORRECTION

PATENT NO. : 4,321,918

DATED : March 30, 1982

INVENTOR(S) : William T. Clark II

It is certified that error appears in the above-identified patent and that said Letters Patent is hereby corrected as shown below:

On the title page

After [76] Inventor:, delete "William T. Clark II", insert -- William T. Clark, III--.

Signed and Sealed this

Nineteenth Day of July 1983

[SEAL]

Attest:

GERALD J. MOSSINGHOFF

Attesting Officer    Commissioner of Patents and Trademarks

REEXAMINATION CERTIFICATE (243rd)

United States Patent [19]

Clark, II

[11] B1 4,321,918

[45] Certificate Issued Sep. 4, 1984

[54] PROCESS FOR SUPPRESSING IMMUNITY TO TRANSPLANTS

[76] Inventor: William T. Clark, II, 6 Davis Blvd., New Orleans, La. 70121

Reexamination Request:
No. 90/000,421, Jul. 15, 1983

Reexamination Certificate for:
Patent No.: 4,321,918
Issued: Mar. 30, 1982
Appl. No.: 87,576
Filed: Oct. 23, 1979

Certificate of Correction issued Mar. 30, 1982.

[51] Int. Cl.$^3$ .............................................. A61M 1/03
[52] U.S. Cl. ...................................... 604/4; 128/362; 604/20
[58] Field of Search ............... 604/5, 20, 21; 128/362, 128/395, 396, DIG. 3; 250/430, 432 R, 435, 437

[56] References Cited

PUBLICATIONS

Persson et al, "Transplantation", vol. 7, No. 6, Jun. 1963, pp. 534–544.
Weeke et al, "Transplantation Proceedings", vol. III, No. 1, Mar. 1971, pp. 387–390.
Hagenbeek et al, "Radiation Research", vol. 80, 1979, pp. 198–207.
Oliver et al, "British Journal of Hafmotology", vol. 10, 1964, pp. 181–192.
Weeke, "Acta Medica, Scandinavica", vol. 195, 1974, pp. 149–154, pp. 485–499.
Rosengren et al, "Scandanavian Journal of Urology & Nephrology", vol. 2, 1968, pp. 58–61.
Gelin et al, "Scandanavian Journal of Urology & Nephrology", vol. 2, 1968, pp. 1–13.
Birkeland, "Acta Medica Scandinavica", vol. 199, 1976, pp. 157–166.
Birkeland, "International Archives of Allergy & Applied Immunology", vol. 57, 1978, pp. 425–434.
Maginn et al, "British Journal of Radiology", vol. 41, Feb. 1968, pp. 127–133.
Felsburg et al, "Journal of Immunology", vol. 116, 1976, pp. 1110–1114.
Felsburg et al, "Journal of Immunology", vol. 118, No. 1, 1977, pp. 62–66.
Merrick et al, "Transplantation", vol. 4, 1966, p. 541.
Hume et al, "Transplantation", vol. 5, No. 1, Part 2, 1967, pp. 1174–1191.
Murray et al, "Annals of Surgery", vol. 168, No. 3, Sep. 1968, pp. 416–435.
Wolf et al, "Journal of the American Medical Association", vol. 194, No. 10, Dec. 6, 1965, pp. 1119–1121.
Wolf et al, "Surgery, Gynecology & Obstetrics", vol. 122, 1966, pp. 1262–1268.
Chanana et al, "Radiation Research", vol. 27, 1966, pp. 330–346.
Joel et al, "Transplantation", vol. 5, No. 4, Part 2, Jul. 1967, pp. 1192–1197.
Anderson et al, "Journal of Immunology", vol. 118, No. 4, 1977, pp. 1191–1200.
Birkeland, "Cryobiology", vol. 13, 1976, pp. 433–441.
Fudenberg et al, "Basic & Clinical Immunology," 3rd ed., Chapter 27, 1980, pp. 384–388.
Steinmuller, "Transplantation", vol. 26, No. 1, Jul. 1978, pp. 2–3.
Oliver et al., "Extracorporeal Irradiation of the Blood: the Mathematical Problem of Dosimetry," *Brit. J. Haematology*, vol. 10, p. 181, (1964).
Persson et al., "Evaluation of Preoperative Extracorporeal Irradiation of Blood in Human Renal Transplantation," *Transplantation*, vol. 7, No. 6, p. 534, (1969).
Weeke et al., "Extracorporeal Irradiation of Blood: Lymphocyte Transformation Tests and Clinical Results after Renal Transplantation," *Transplantation Proceedings*, vol. III, No. 1, p. 387, (Mar. 1971).
Hagenbeek et al., "A Method of Extracorporeal Irradiation of the Blood in the Rat," *Radiation Research*, vol. 80, p. 198, (1979).

*Primary Examiner*—William E. Kamm

[57] ABSTRACT

In order to inhibit rejection of transplants in humans, lymphoctyes are suppressed by limited and closely controlled extracorporeal irradiation of an intensity and duration sufficient to reduce lymphocyte function to from about 10% to about 20% of normal.

REEXAMINATION CERTIFICATE ISSUED UNDER 35 U.S.C. 307.

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-3, 5 and 6 is confirmed.

Claim 4 is determined to be patentable as amended.

4. A process as claimed in claim 3 wherein the total dose *per treatment* is between 24.4 R to 93.3 R.

* * * * *